US012303507B2

(12) United States Patent
Kim et al.

(10) Patent No.: US 12,303,507 B2
(45) Date of Patent: May 20, 2025

(54) PHARMACEUTICAL COMPOSITION OF SINGLE DOSAGE FORM FOR TREATING OR PREVENTING HYPERTENSION AND HYPERLIPIDEMIA

(71) Applicant: Daewoong Pharmaceutical Co., Ltd., Hwaseong-si (KR)

(72) Inventors: Ji Yeon Kim, Seoul (KR); Bo Hoon Kim, Yongin-si (KR)

(73) Assignee: DAEWOONG PHARMACEUTICAL CO., LTD., Hwaseong-si (KR)

( * ) Notice: Subject to any disclaimer, the term of this patent is extended or adjusted under 35 U.S.C. 154(b) by 773 days.

(21) Appl. No.: 17/431,464

(22) PCT Filed: Feb. 26, 2020

(86) PCT No.: PCT/KR2020/002772
§ 371 (c)(1),
(2) Date: Aug. 17, 2021

(87) PCT Pub. No.: WO2020/175922
PCT Pub. Date: Sep. 3, 2020

(65) Prior Publication Data
US 2022/0133720 A1    May 5, 2022

(30) Foreign Application Priority Data

Feb. 26, 2019  (KR) .................. 10-2019-0022739

(51) Int. Cl.
| A61K 31/505 | (2006.01) |
| A61K 9/20 | (2006.01) |
| A61K 9/24 | (2006.01) |
| A61K 9/28 | (2006.01) |
| A61K 31/4178 | (2006.01) |
| A61K 31/4422 | (2006.01) |

(52) U.S. Cl.
CPC .......... *A61K 31/505* (2013.01); *A61K 9/2009* (2013.01); *A61K 9/2077* (2013.01); *A61K 9/209* (2013.01); *A61K 9/284* (2013.01); *A61K 31/4178* (2013.01); *A61K 31/4422* (2013.01)

(58) Field of Classification Search
None
See application file for complete search history.

(56) References Cited

U.S. PATENT DOCUMENTS

2011/0038898 A1* 2/2011 Yada ................ A61K 31/4422
514/223.5
2013/0067664 A1  3/2013 Lu et al.

FOREIGN PATENT DOCUMENTS

| CN | 101247832 A | 8/2008 | |
| EP | 3320903 A1 * | 5/2018 | ............. A61K 31/41 |
| IN | 1919MUN2014 | 7/2015 | |
| KR | 20090065510 A | 6/2009 | |
| KR | 20130030734 A | 3/2013 | |
| KR | 20130111335 A | 10/2013 | |
| KR | 20170007695 A | 1/2017 | |
| KR | 20180120309 A | 11/2018 | |
| WO | 2008032107 A1 | 3/2008 | |
| WO | WO-2008117707 A1 * | 10/2008 | ......... A61K 31/4178 |
| WO | WO-2013147462 A1 * | 10/2013 | ......... A61K 31/4178 |
| WO | WO-2017007287 A1 * | 1/2017 | ............. A61K 31/41 |

OTHER PUBLICATIONS https://www.drugs.com/compare/olmesartan-vs-valsartan (Year: 2023).*
Translated WO 2017007287 A1 (Year: 2017).*
Translated WO-2008117707 (Year: 2008).*
https://go.drugbank.com/drugs/DB00275 (Year: 2020).*
Oh et al., "Pharmacokinetic comparison of a fixed-dose combination versus concomitant administration of amlodipine, olmesartan, and rosuvastatin in healthy adult subjects," Drug Design, Development and Therapy, vol. 13, pp. 991-997 (2019).
Oh et al., "Pharmacokinetic comparison of a fixed-dose combination versus concomitant administration of fimasartan, amlodipine, and rosuvastatin using partial replicated design in healthy adult subjects," Drug Design, Development and Therapy, vol. 12, pp. 1157-1164 (2018).
Park et al., "Efficacy and safety of fixed-dose combination therapy with olmesartan medoxomil and rosuvastatin in Korean patients with mild to moderate hypertension and dyslipidemia: an 8-week, multicenter, randomized, double-blind, factorial design study (Olsta-D RCT: OLmesartan rosuvaSTAtin from Daewoong)," Drug Design, Development and Therapy, vol. 10, pp. 2599-2609 (2016).
Sole et al., "Olmesartan Plus Amlodipine Compared to Valsartan Plus Amlodipine Reduce More Left Ventricular Hypertrophy and Arterial Stiffness in Mild to Moderate Hypertensive Patients," Journal of Hypertension, vol. 33, e-Supplement 1, e 323, p. 21.18 (2015).
International Search Report issued Jul. 31, 2020 in International Application No. PCT/KR2020/002772.
Written Opinion issued Jul. 31, 2020 in International Application No. PCT/KR2020/002772.
Office Action issued Oct. 21, 2021 in IN Application No. 202137037101.
Pabari et al., "Effect of a Disintegration Mechanism on Wetting, Water Absorption, and Disintegration Time of Orodispersible Tablets," Journal of Young Pharmacists, vol. 4, No. 3, pp. 157-163 (2012).
Extended European Search Report issued Nov. 3, 2022 in EP Application No. 20763090.6.
Office Action issued Sep. 5, 2022 in CN Application No. 202080017133.3 (with Partial English Translation).

* cited by examiner

*Primary Examiner* — Andrew S Rosenthal
*Assistant Examiner* — Danielle Kim
(74) *Attorney, Agent, or Firm* — Panitch Schwarze Belisario & Nadel LLP

(57) ABSTRACT

The present invention provides a pharmaceutical composition of a single dosage form for treating hypertension and hyperlipidemia. According to the present invention, compartments comprising a drug are formulated in separate forms so as to solve problems related to the dissolution and absorption of the drug due to drug interaction, and a biologically equivalent preparation can be obtained when compared to conventional single preparation.

11 Claims, 6 Drawing Sheets

[Fig. 1]
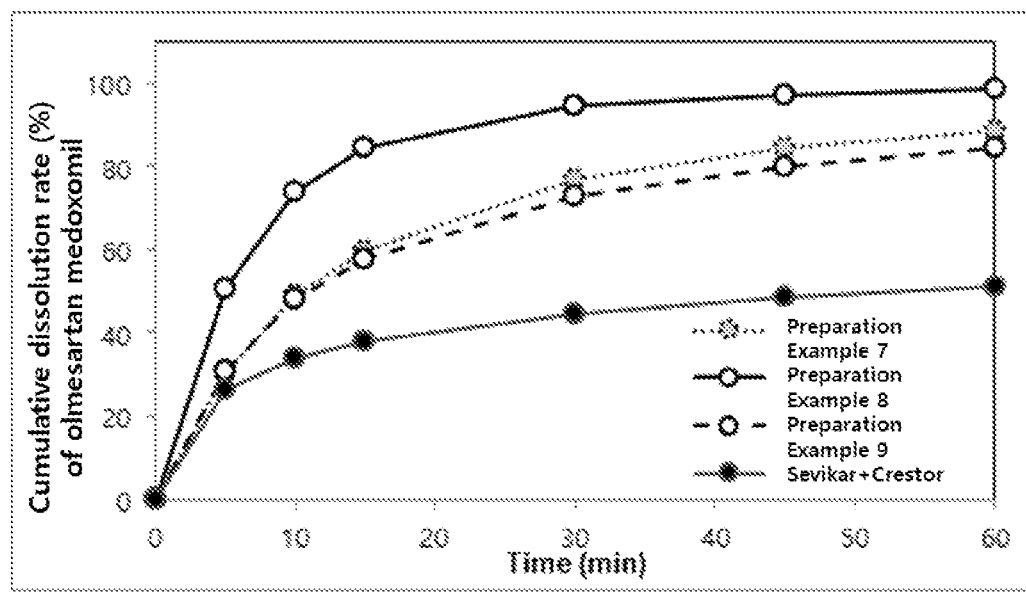
[Fig. 2]
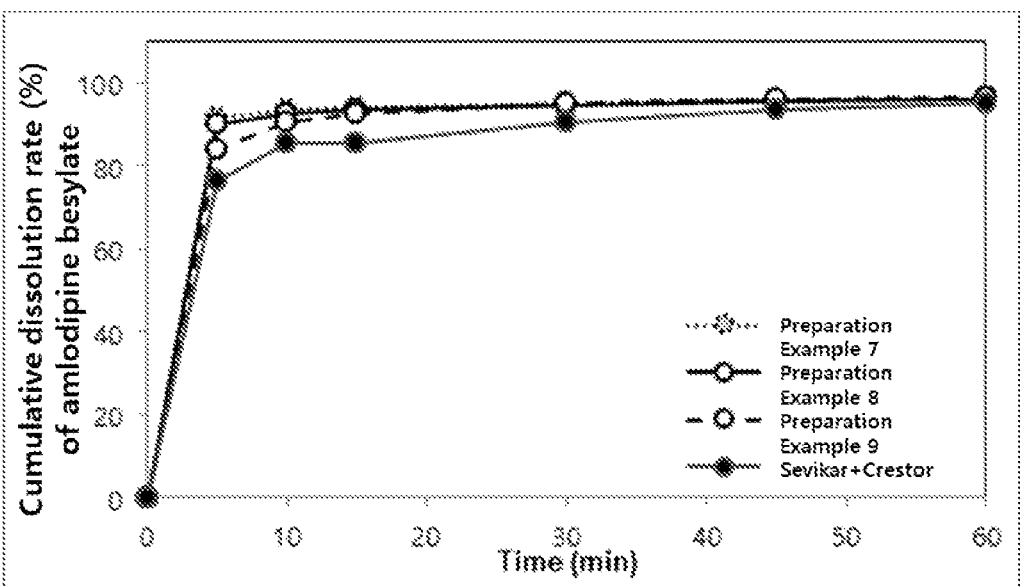

[Fig. 3]
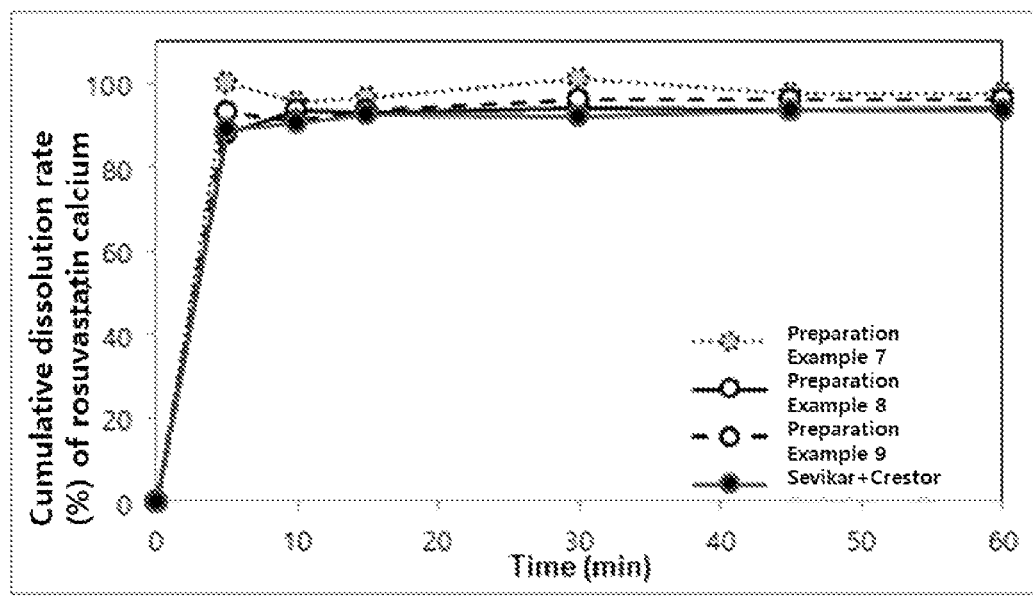
[Fig. 4]
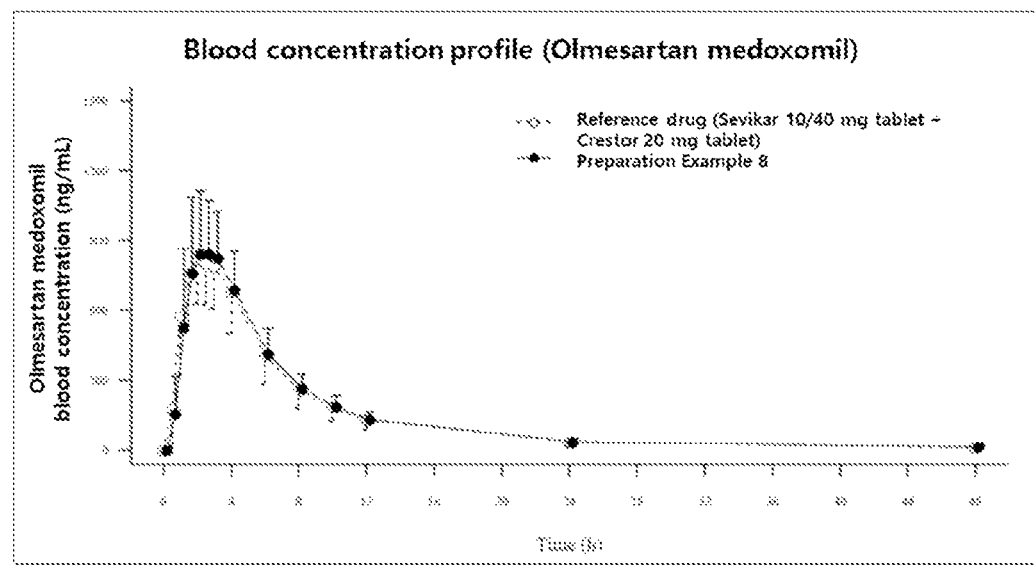

[Fig. 5]
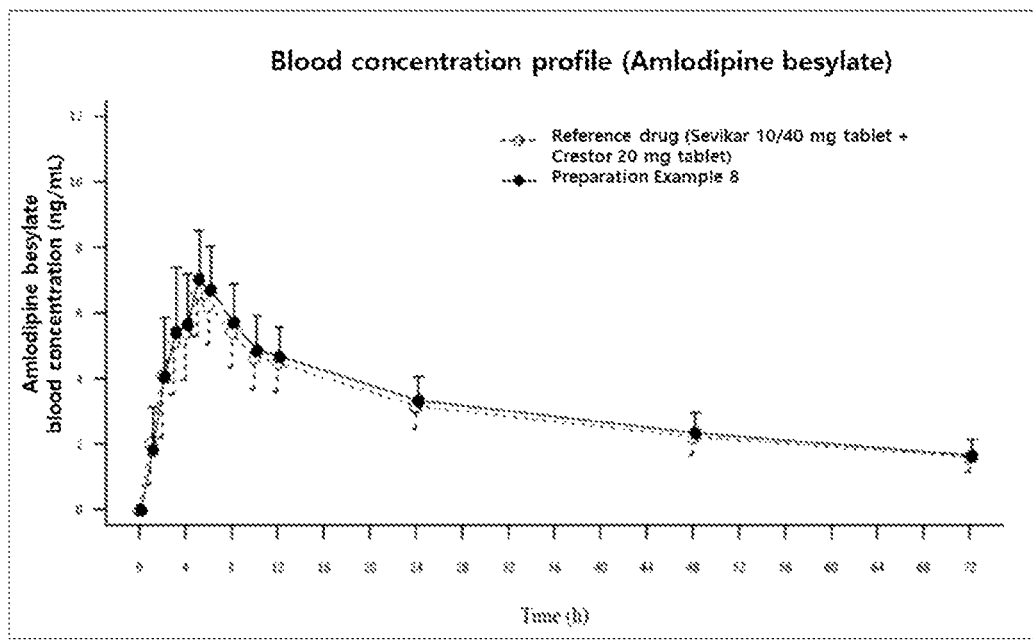
[Fig. 6]
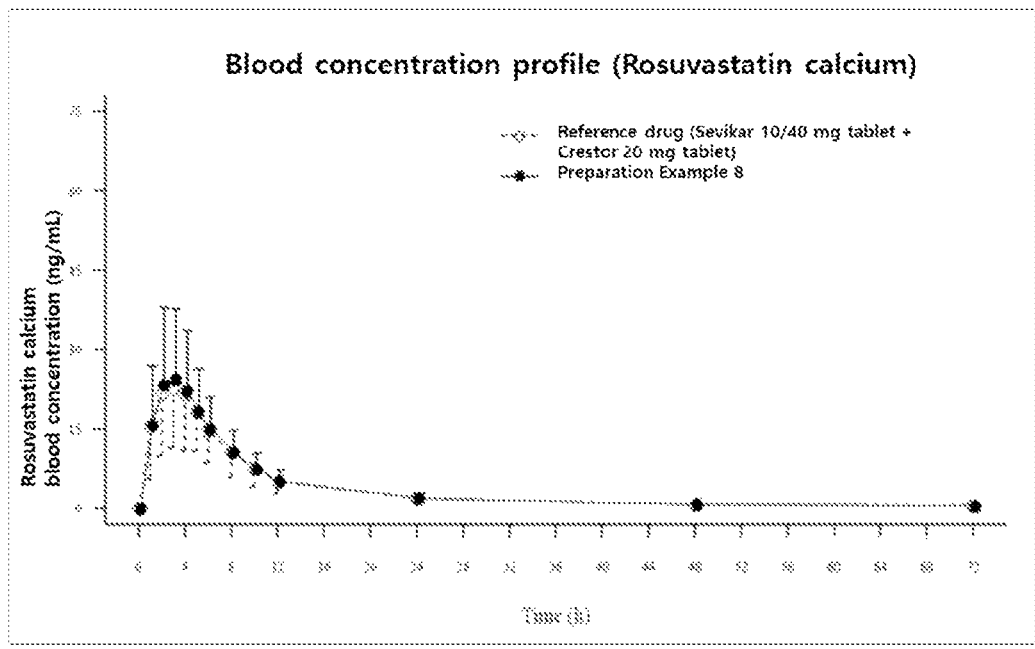

[Fig. 7]
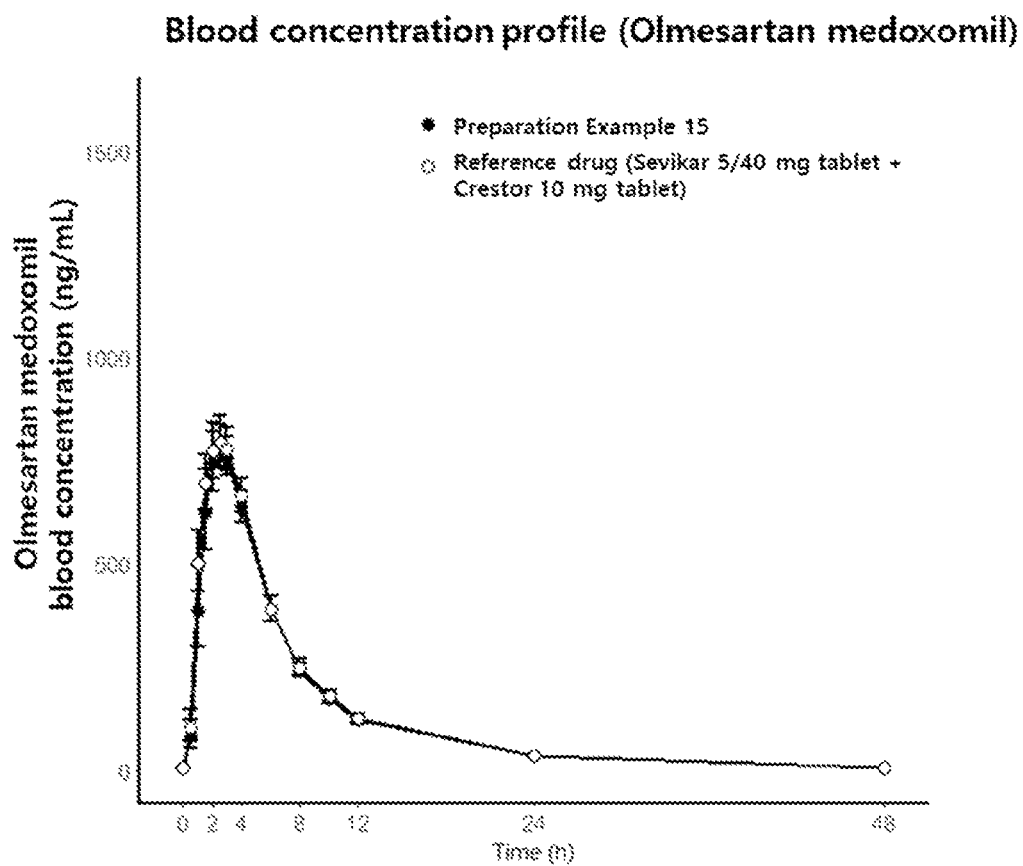

[Fig. 8]
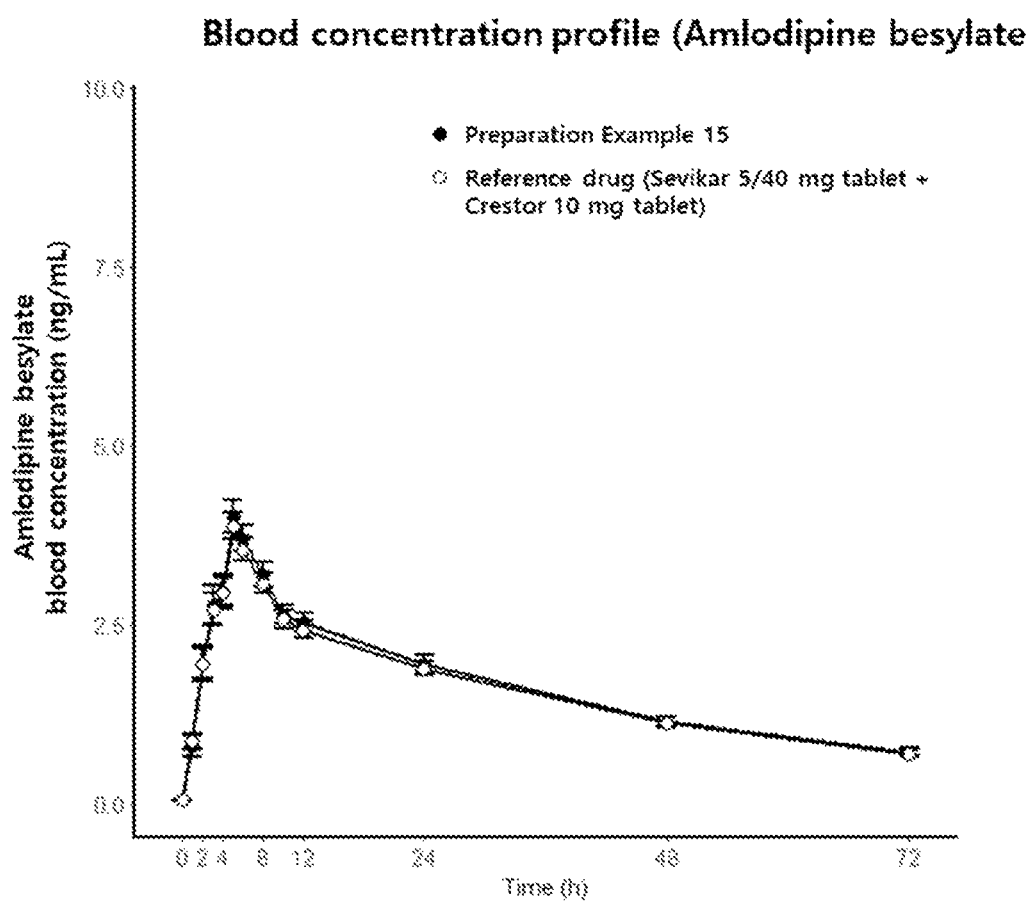

[Fig. 9]
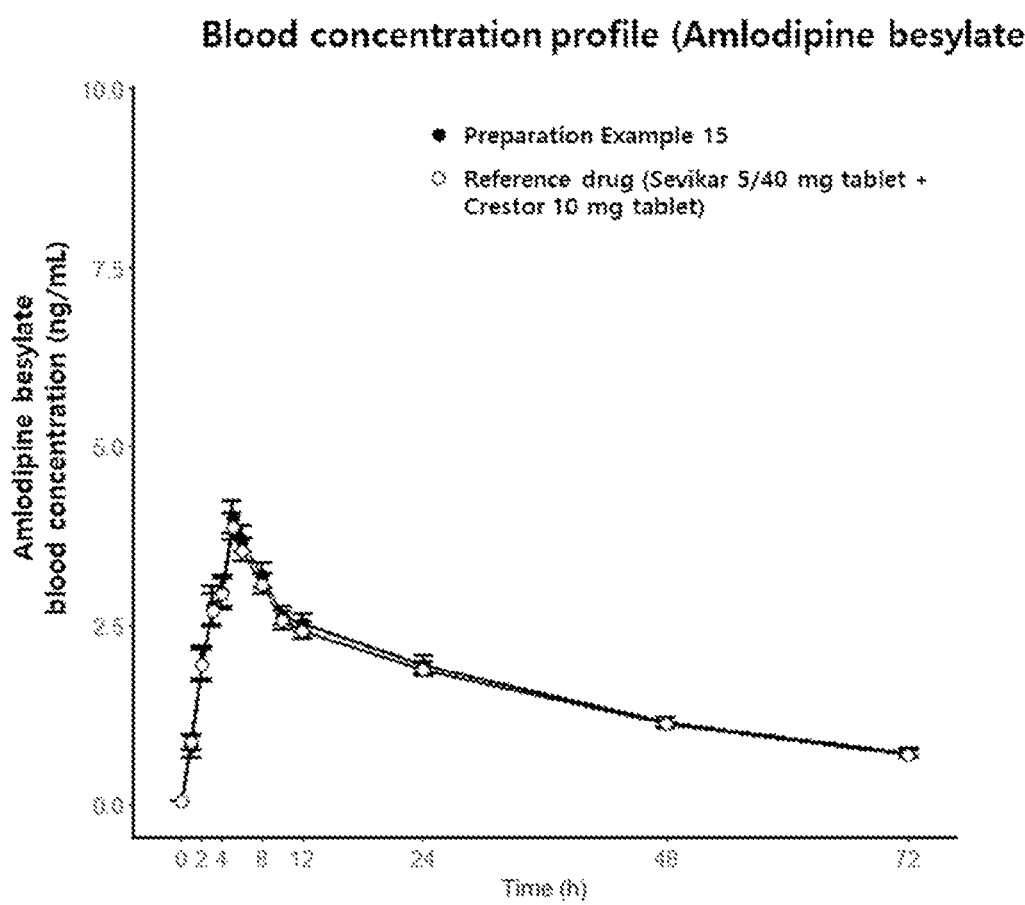

PHARMACEUTICAL COMPOSITION OF SINGLE DOSAGE FORM FOR TREATING OR PREVENTING HYPERTENSION AND HYPERLIPIDEMIA

CROSS-REFERENCE TO RELATED APPLICATIONS

This application is a Section 371 of International Application No. PCT/KR2020/002772, filed Feb. 26, 2020, which was published in the Korean language on Sep. 3, 2020 under International Publication No. WO 2020/175922 A1, which claims priority under 35 U.S.C. § 119(b) to Korean Application No. 10-2019-0022739, filed on Feb. 26, 2019, the disclosures of which are incorporated herein by reference in their entireties.

TECHNICAL FIELD

The present invention relates to a pharmaceutical composition of a single dosage form for treating hypertension and hyperlipidemia.

BACKGROUND ART

Since there are a large number of patients suffering from hypertension and hyperlipidemia, therapeutic drugs for these diseases are simultaneously prescribed to many patients. Since it is advantageous for patients to be prescribed a single dosage form, for example, Caduet™, which is a combination drug of atorvastatin and amlodipine, is being prescribed to patients as a combination drug for the treatment of hypertension and hyperlipidemia.

Olmesartan medoxomil is an excellent angiotensin II receptor blocker (ARB), and is known to be useful as a drug for the treatment or prevention of hypertension, a heart disease, and the like. Olmesartan medoxomil is currently sold under the trade name Olmetec™.

Amlodipine is a calcium channel blocker (CCB) and is known to be useful as a drug for the treatment or prevention of hypertension, a heart disease, and the like. Amlodipine is currently sold under the trade name Norvas™.

Meanwhile, rosuvastatin is a HMG-CoA reductase inhibitor, is used for the treatment of hypercholesterolemia, hyperlipoproteinemia, and atherosclerosis, and is currently sold under the trade name Crestor™.

Olmesartan medoxomil is particularly useful for renin-dependent hypertension as an angiotensin II receptor blocker, and amlodipine is useful for renin-independent hypertension because amlodipine has a natriuretic effect in addition to a calcium channel dilation action. Therefore, a combination drug of olmesartan medoxomil and amlodipine was developed to treat hypertension regardless of the etiology, and is currently sold under the trade name Sevikar™.

Meanwhile, the present applicants have disclosed a combination drug containing olmesartan medoxomil and rosuvastatin through the Korean patent application No. 10-2013-0030734. Currently, the combination drug containing olmesartan medoxomil and rosuvastatin is sold under the trade name Olostar™.

As described above, a combination drug containing olmesartan medoxomil and amlodipine and a combination drug containing olmesartan medoxomil and rosuvastatin were developed, respectively, but a combination drug containing olmesartan medoxomil, amlodipine, and rosuvastatin has not been developed to date.

RELATED ART DOCUMENT

Patent Document (Patent Document 1) Korean Patent Application No. 10-2013-0030734

DISCLOSURE

Technical Problem

Olmesartan medoxomil and rosuvastatin show mutual interference or interaction while a combination drug of a single dosage form containing olmesartan medoxomil and rosuvastatin was developed through conventional prior invention (No. 10-2013-0030734) of the present applicants, and it was confirmed that even though a separate compartmentalized combination drug is prepared in order to prevent the interference or interaction, bioequivalence with each single preparation is secured only when a specific disintegrant is used.

Meanwhile, when the two drugs, olmesartan medoxomil and amlodipine, are also used in combination, it is known that the dissolution rate of olmesartan medoxomil decreases due to drug interaction.

Therefore, an object of the present invention is to develop, as a pharmaceutical composition of a single dosage form containing olmesartan medoxomil, amlodipine, and rosuvastatin, a combination drug in which each drug satisfies all requirements associated with a drug dissolution rate and bioequivalence.

Technical Solution

As a result of performing tests by designing various preparations in order to develop a combination drug of a single dosage form containing olmesartan medoxomil, amlodipine, and rosuvastatin, the present inventors completed the present invention.

The present invention provides a pharmaceutical composition of a single dosage form, comprising: a compartment comprising olmesartan medoxomil and amlodipine or a salt thereof; and a compartment comprising rosuvastatin or a salt thereof, wherein the compartments are formulated in separate forms.

As a result of formulating a pharmaceutical composition containing olmesartan medoxomil, amlodipine or a salt thereof, and rosuvastatin or a salt thereof by separating the pharmaceutical composition into a compartment comprising olmesartan medoxomil and amlodipine or a salt thereof; and a compartment comprising rosuvastatin or a salt thereof, the present inventors confirmed that the pharmaceutical composition exhibits a dissolution pattern similar to that of a reference drug by preventing a drug interaction between olmesartan medoxomil and rosuvastatin and a drug interaction between olmesartan medoxomil and amlodipine.

Further, the present inventors confirmed that when compared to a single preparation containing olmesartan medoxomil and amlodipine during an in vitro comparative dissolution test under specific dissolution solution conditions, a preparation which is biologically equivalent to a single preparation containing olmesartan medoxomil and amlodipine is obtained only when the dissolution rate of olmesartan medoxomil is designed at a level as high as a non-equivalent level in terms of pharmaceutical equivalence. That is, a combination drug composition according to the present invention has a higher initial olmesartan medoxomil dissolution rate than a conventional combination drug of a single dosage form containing olmesartan medoxomil and amlodipine.

A pharmaceutical composition of the present invention may have a separate compartment dosage form, for example, a bilayer tablet, a tablet-in-tablet, a mini tablet- and/or a pellet-containing capsule.

In an exemplary embodiment of the present invention, the pharmaceutical composition of the present invention has a dosage form of a bilayer tablet including a layer containing olmesartan medoxomil and amlodipine or a salt thereof and a layer containing rosuvastatin or a salt thereof. In another exemplary embodiment, the pharmaceutical composition of the present invention has a dosage form of a tablet-in-tablet including a core containing rosuvastatin or a salt thereof and a shell containing olmesartan medoxomil and amlodipine or a salt thereof. Alternatively, the pharmaceutical composition of the present invention has a dosage form of a tablet-in-tablet including a core containing olmesartan medoxomil and amlodipine or a salt thereof and a shell containing rosuvastatin or a salt thereof. In still another exemplary embodiment, the pharmaceutical composition of the present invention may have a dosage form of a capsule containing a mini tablet containing rosuvastatin or a salt thereof and a mini tablet containing olmesartan medoxomil and amlodipine or a salt thereof. In yet another exemplary embodiment, the pharmaceutical composition of the present invention may have a dosage form of a capsule containing a mini tablet containing rosuvastatin or a salt thereof and a pellet or powder containing olmesartan medoxomil and amlodipine or a salt thereof. Alternatively, the pharmaceutical composition of the present invention may have a dosage form of a capsule containing a mini tablet containing olmesartan medoxomil and amlodipine or a salt thereof and a pellet or powder containing rosuvastatin or a salt thereof. In yet another exemplary embodiment, the pharmaceutical composition of the present invention may have a dosage form of a capsule containing a pellet containing olmesartan medoxomil and amlodipine or a salt thereof and a pellet containing rosuvastatin or a salt thereof.

As a peculiar point, it is preferred that a compartment comprising olmesartan medoxomil and amlodipine or a salt thereof contain dibasic calcium phosphate dihydrate. As can be confirmed in the following Examples, excellent results could be obtained in a comparative dissolution test and a bioequivalent test when dibasic calcium phosphate dihydrate was included in a compartment comprising olmesartan medoxomil and amlodipine or a salt thereof. In contrast, when dibasic calcium phosphate dihydrate was included only in a rosuvastatin compartment, satisfiable results could not be obtained in the comparative dissolution test and the bioequivalent test even though the content of the dibasic calcium phosphate dihydrate was increased. In addition, a preparation containing anhydrous dibasic calcium phosphate instead of dibasic calcium phosphate dihydrate in a compartment comprising olmesartan medoxomil and amlodipine or a salt thereof also had a smaller deviation than a reference drug with respect to olmesartan medoxomil and a slightly bigger deviation than the reference drug with respect to amlodipine and rosuvastatin when compared to the case where dibasic calcium phosphate dihydrate was used in the comparative dissolution test. However, the preparation was shown to be non-equivalent to the reference drug in the bioequivalent test.

Therefore, a preferred exemplary embodiment of the present invention contains dibasic calcium phosphate dihydrate in a compartment comprising olmesartan medoxomil and amlodipine or a salt thereof. The dibasic calcium phosphate dihydrate may be included in a range of 1 to 30 parts by weight, preferably 1 to 20 parts by weight, for example, 10 to 20 parts by weight, based on total 100 parts by weight of a compartment comprising olmesartan medoxomil and amlodipine or a salt thereof.

In an exemplary embodiment of the present invention, it may be preferred that the compartment comprising olmesartan medoxomil and amlodipine or a salt thereof contains two or more disintegrants selected from the group consisting of pregelatinized starch, croscarmellose sodium, crospovidone, carboxymethyl cellulose calcium, sodium starch glycolate, copovidone, and complex silicate.

The disintegrant may be included in an amount of 5 to 60 parts by weight based on total 100 parts by weight of the compartment comprising olmesartan medoxomil and amlodipine or a salt thereof, but the amount is not limited thereto. Specifically, pregelatinized starch, croscarmellose sodium, and crospovidone may be included in an amount of 4 to 40 parts by weight, 1 to 20 parts by weight, and 1 to 20 parts by weight, respectively, based on total 100 parts by weight of the compartment comprising olmesartan medoxomil and amlodipine or a salt thereof. Likewise, each of carboxymethyl cellulose calcium, sodium starch glycolate, copovidone, and complex silicate may be included in an amount of 1 to 40 parts by weight based on total 100 parts by weight the compartment comprising olmesartan medoxomil and amlodipine or a salt thereof.

The compartment comprising olmesartan medoxomil and amlodipine or a salt thereof may contain suitable excipients and additives in addition to the dibasic calcium phosphate dihydrate and the disintegrant. Examples of the excipient include lactose (including a hydrate thereof), dextrin, mannitol, sorbitol, starch, microcrystalline cellulose [for example, Celphere™], silicified microcrystalline cellulose [for example, Prosolv™], calcium carbonate, sugars, or a mixture thereof. Examples of other additives include a binder, a glidant, a colorant, and the like. The binder includes polyvinylpyrrolidone, copovidone, gelatin, starch, sucrose, methylcellulose, ethyl cellulose, hydroxypropylcellulose, a hydroxypropylalkylcellulose (for example, hydroxypropylmethylcellulose), and a mixture thereof. The glidant includes stearic acid, a stearate (for example, magnesium stearate), talc, corn starch, carnauba wax, hard anhydrous silicic acid, magnesium silicate, synthetic aluminum silicate, hardened oil, white lead, titanium oxide, microcrystalline cellulose, Macrogol 4000 and 6000, isopropyl myristate, calcium hydrogen phosphate, and a mixture thereof.

Meanwhile, in an exemplary embodiment of the present invention, it is preferred that the compartment comprising rosuvastatin or a salt thereof contains two or more disintegrants selected from the group consisting of crospovidone, low-substituted hydroxypropylcellulose, croscarmellose sodium, and carboxymethyl cellulose calcium. The disintegrant may be included in a range of 2 to 20 parts by weight based on total 100 parts by weight of the compartment comprising rosuvastatin or a salt thereof, but the range is not limited thereto. Specifically, each of crospovidone, low-substituted hydroxypropylcellulose, croscarmellose sodium, and carboxymethyl cellulose calcium may be included in an amount of 1 to 20 parts by weight, preferably 1 to 10 parts by weight based on total 100 parts by weight of a compartment comprising rosuvastatin or a salt thereof. In an exemplary embodiment of the present invention, the compartment comprising rosuvastatin or a salt thereof contains crospovidone and croscarmellose sodium as a disintegrant in a range of 2 to 20 parts by weight based on total 100 parts by weight of a compartment comprising rosuvastatin or a salt thereof. In this case, each of crospovidone and croscarmellose sodium may be included in an amount of 1 to 20 parts by weight, for example, 1 to 10 parts by weight based on total 100 parts by weight of a compartment comprising rosuvastatin or a salt thereof.

The compartment comprising rosuvastatin or a salt thereof may contain suitable excipients and additives in addition to the disintegrant. Examples of the excipient include lactose (including a hydrate thereof), dextrin, mannitol, sorbitol, starch, microcrystalline cellulose [for example, Celphere™], silicified microcrystalline cellulose [for example, Prosolv™], dibasic calcium phosphate (including a hydrate thereof), anhydrous dibasic calcium phosphate, calcium carbonate, sugars, or a mixture thereof. Examples of other additives include a binder, a glidant, a colorant, and the like. The binder includes polyvinylpyrrolidone, copovidone, gelatin, starch, sucrose, methylcellulose, ethylcellulose, hydroxypropylcellulose, a hydroxypropylalkylcellulose (for example, hydroxypropylmethylcellulose), and a mixture thereof. The glidant includes stearic acid, a stearate (for example, magnesium stearate), talc, corn starch, carnauba wax, hard anhydrous silicic acid, magnesium silicate, synthetic aluminum silicate, hardened oil, white lead, titanium oxide, microcrystalline cellulose, Macrogol 4000 and 6000, isopropyl myristate, calcium hydrogen phosphate, and a mixture thereof.

In an exemplary embodiment, the pharmaceutical composition of the present invention in the form of a bilayer tablet may be prepared by preparing each of an olmesartan medoxomil/amlodipine besylate portion mixture and a rosuvastatin calcium portion mixture by a typical method, and then compressing the mixtures using a bilayer tablet machine.

In another exemplary embodiment, the pharmaceutical composition of the present invention in the form of a bilayer tablet may be prepared by preparing each of olmesartan medoxomil/amlodipine besylate granules and rosuvastatin granules, and then compressing the granules using a bilayer tablet machine. The olmesartan medoxomil/amlodipine besylate granules and rosuvastatin granules may be prepared by a dry granulation or wet granulation process using a typical method.

A film coating layer such as Opadry™ may be formed on an obtained bilayer tablet, if necessary.

In still another exemplary embodiment, the pharmaceutical composition of the present invention in the form of a tablet-in-tablet may be prepared by forming a core tablet containing rosuvastatin, then forming a film coating layer as described above, if necessary, and then compressing the core tablet together with olmesartan medoxomil granules using a single tablet press (EKO, Korsch), and the like. Here, the core tablet containing rosuvastatin may be prepared, for example, by preparing a rosuvastatin calcium portion as dry granules or wet granules, and then compressing the rosuvastatin calcium portion with a continuous tablet press (Piccola D-8, RIVA) or the like. A film coating layer such as Opadry™ may also be formed on an obtained tablet-in-tablet, if necessary.

In yet another exemplary embodiment, the pharmaceutical composition of the present invention in the form of a dosage form containing a mini tablet may be prepared by preparing a mini tablet containing olmesartan medoxomil/amlodipine or a salt thereof and/or a mini tablet containing rosuvastatin or a salt thereof, and filling a capsule with the mini tablet(s) together with a mini tablet, pellet, or powder containing rosuvastatin or a salt thereof, or a mini tablet, pellet, or powder containing olmesartan medoxomil/amlodipine or a salt thereof.

In yet another exemplary embodiment, the pharmaceutical composition of the present invention in the form of a pellet-containing capsule may be prepared by preparing each of an olmesartan medoxomil/amlodipine besylate pellet and a rosuvastatin pellet, and then filling a capsule with the pellets.

Here, the rosuvastatin pellet may be prepared, for example, by putting beads such as non-pareil beads into a fluidized bed coater and coating the beads with a coating solution prepared by dissolving rosuvastatin calcium, an excipient (diluent), a binder, and a disintegrant in an appropriate solvent, for example, a mixed solvent of water and methanol. The viscosity of the coating solution is preferably in a range of 5 mPa·s to 100 mPa·s. Further, the olmesartan medoxomil pellet may also be prepared similarly by putting non-pareil beads into a fluidized bed coater and coating the beads with a coating solution prepared by dissolving olmesartan medoxomil, an excipient (diluent), and a binder in an appropriate solvent, for example, a mixed solvent of water and methanol.

When the pharmaceutical composition of the present invention is a tablet, the pharmaceutical composition may be coated with a coating agent. In an exemplary embodiment, the pharmaceutical composition of the present invention may be a bilayer tablet or tablet-in-tablet coated with a coating agent. The coating agent, for example, a film coating agent may contain a typical polymer such as Opadry™. As the film coating agent, polyvinyl alcohol (PVA), a polyvinyl alcohol copolymer, hydroxypropyl methylcellulose (HPMC), and the like may be specifically used. Examples of the polyvinyl alcohol copolymer may be a PVA/Macrogol grafted polymer, but are not limited thereto. In an exemplary embodiment, the pharmaceutical composition of the present invention may be a bilayer tablet or tablet-in-tablet coated with polyvinyl alcohol or a polyvinyl alcohol copolymer. An amount of film coating agent used is preferably a minimum amount capable of providing the optimum preparation size, and is not particularly limited.

Meanwhile, in the present invention, the salt of amlodipine contains a typical pharmaceutically acceptable salt, and for example, besylate, hydrochloride, hydrobromide, fumarate, citrate, tartrate, maleate, cansylate, lactate, mesylate, camsylate, gluconate and the like may be used. Preferably, amlodipine besylate may be used. Meanwhile, the salt of rosuvastatin includes a typical pharmaceutically acceptable salt, and for example, a calcium salt, hydrochloride, hydrobromide, sulfate, phosphate, acetate, malate, fumarate, lactate, tartrate, citrate, gluconate, besylate, camsylate and the like can be used. Preferably, rosuvastatin calcium may be used.

Although not limited to this, the particle sizes of olmesartan medoxomil, amlodipine or a salt thereof, and rosuvastatin or a salt thereof may be appropriately adjusted.

When micronization of the drug particle size is required, particles may be crushed using a typical mill such as a Z-mill, a hammer mill, a ball mill, and a fluid energy mill. In addition, the particle size of the drug may be subdivided using a sieving method performed using a sieve or a size classification method such as air current classification. A method of adjusting a desired particle size is well known in the art. For example, reference the following document: [Pharmaceutical dosage forms: volume 2, 2nd edition, Ed.: H. A. Lieberman, L. Lachman, J. B. Schwartz (Chapter 3: SIZE REDUCTION)].

The particle size of a drug in the present specification is expressed based on a particle size distribution such as d(X)=Y (where X and Y are positive numbers). d(X)=Y means that when a particle size distribution of a drug obtained by measuring the particle size of any drug in a preparation is represented by a cumulative curve, a particle diameter at a point where X % (% is calculated based on the number, volume, or weight) accumulated in the ascending order of the particle size is Y. For example, d(10) represents a diameter of a particle at a point where a particle size of a drug is accumulated in the ascending order and becomes 10%, d(50) represents a diameter of a particle at a point where a particle size of a drug is accumulated in the ascending order and becomes 50%, and d(90) represents a diameter of a particle at a point where a particle size of a drug is accumulated in the ascending order and becomes 90%.

Whether the particle size distribution d(X) represents a percentage of the total cumulative particles on the basis of number, volume, or weight depends on the method used to measure the particle size distribution. A method of measuring the particle size distribution and the associated % type are known in the art. For example, when the particle size distribution is measured by a well-known laser diffraction method, the X value in d(X) represents a percentage calculated by the volume average. Those skilled in the art are well aware that the results of measuring the particle size distribution obtained by a particular method may be associated with those obtained from other techniques based on experience by typical experiments. For example, the laser diffraction method provides a volume average particle size in response to the volume of the particles, which corresponds to a weight average particle size when the density is constant.

In the present invention, the particle size distribution of the drug particles may be measured using a commercially available device based on the laser diffraction-scattering method based on the Mie theory. For example, the particle size distribution of the drug particles is measured using a commercially available device such as a Mastersizer laser diffractometer manufactured by Malvern Instruments Ltd. In this device, when particles are irradiated with a helium neon laser beam and a blue light emitting diode, scattering occurs, so that a light scattering pattern appears on a detector, and a particle size distribution is obtained by analyzing this light scattering pattern according to the Mie theory. The measurement method can be either a dry method or a wet method.

In the case of olmesartan medoxomil, D(90) may be 5 to 45 μm, preferably 10 to 30 μm. In the case of amlodipine or a salt thereof, D(90) may be 5 to 100 μm, preferably 10 to 60 μm, and more preferably 15 to 45 μm. In the case of rosuvastatin or a salt thereof, D(90) may be 5 to 50 μm, preferably 15 to 40 μm, and more preferably 20 to 35 μm. When olmesartan medoxomil, amlodipine or a salt thereof, and rosuvastatin or a salt thereof are within the above ranges, it may be suitable to indicate a dissolution rate of a drug, which is at a level equivalent to a reference drug, and a blood concentration-area under the time curve (AUC) and a maximum blood concentration ($C_{max}$) at levels biologically equivalent to the reference drug.

The pharmaceutical composition of the present invention may be used in a patient who needs to be simultaneously administered olmesartan medoxomil and rosuvastatin. Currently, a combination drug of olmesartan medoxomil and amlodipine is used for the treatment of essential hypertension in which blood pressure is not appropriately regulated by amlodipine or olmesartan medoxomil single therapy. Further, rosuvastatin is used for the treatment of hypercholesterolemia, hyperlipoproteinemia, and/or atherosclerosis. Information on each drug is already well known.

The present invention provides a pharmaceutical composition in which the dissolution rate of amlodipine or a salt thereof is equivalent to the dissolution rate of amlodipine or a salt thereof of a Sevikar™ tablet. Here, whether or not the dissolution rate shows the equivalent level may be judged in accordance with drug equivalence test management regulations.

The present invention also provides a pharmaceutical composition in which the dissolution rate of rosuvastatin or a salt thereof is equivalent to the dissolution rate of rosuvastatin of a Crestor™ tablet.

Olmesartan medoxomil and amlodipine or a salt thereof in the pharmaceutical composition of the present invention are characterized by showing a blood concentration-area under the time curve (AUC) and a maximum blood concentration ($C_{max}$) at levels biologically equivalent to a Sevikar™ tablet having the same active ingredient dose.

Furthermore, a rosuvastatin calcium salt in the pharmaceutical composition of the present invention is characterized by showing a blood concentration-area under the time curve (AUC) and a maximum blood concentration ($C_{max}$) at levels biologically equivalent to a Crestor™ tablet having the same active ingredient dose.

Therefore, the pharmaceutical composition of the present invention is particularly useful for a patient who requires combined therapy of amlodipine and olmesartan medoxomil and simultaneously requires administration of rosuvastatin.

In the pharmaceutical composition of the present invention, the active ingredients olmesartan medoxomil, amlodipine or a salt thereof, and rosuvastatin or a salt thereof may be used in a therapeutically effective amount. The therapeutically effective amount may vary depending on the symptoms, age, and body weight of the patient, severity of the disease, and the like.

Olmesartan medoxomil may be used in a content of about 5 mg to about 80 mg, preferably about 10 mg to about 40 mg, based on, for example, a unit preparation (that is, a unit administration form), but the content is not limited thereto. Further, amlodipine or a salt thereof may be used in a content of about 2.5 mg to 10 mg based on a unit preparation (that is, a unit administration form). In addition, rosuvastatin or a salt thereof may be used in a content of about 2.5 mg to about 40 mg, preferably about 5 mg to about 20 mg, based on a unit preparation (that is a unit administration form).

In an exemplary embodiment, the pharmaceutical composition of the present invention may contain 40 mg of olmesartan medoxomil, 10 mg of amlodipine or a salt thereof, and 20 mg of rosuvastatin or a salt thereof.

In another exemplary embodiment, the pharmaceutical composition of the present invention may contain 40 mg of olmesartan medoxomil, 10 mg of amlodipine or a salt thereof, and 10 mg of rosuvastatin or a salt thereof.

In still another exemplary embodiment, the pharmaceutical composition of the present invention may contain 40 mg of olmesartan medoxomil, 5 mg of amlodipine or a salt thereof, and 10 mg of rosuvastatin or a salt thereof.

In yet another exemplary embodiment, the pharmaceutical composition of the present invention may contain 40 mg of olmesartan medoxomil, 5 mg of amlodipine or a salt thereof, and 5 mg of rosuvastatin or a salt thereof.

In yet another exemplary embodiment, the pharmaceutical composition of the present invention may contain 20 mg of olmesartan medoxomil, 5 mg of amlodipine or a salt thereof, and 10 mg of rosuvastatin or a salt thereof.

In yet another exemplary embodiment, the pharmaceutical composition of the present invention may contain 20 mg of olmesartan medoxomil, 5 mg of amlodipine or a salt thereof, and 5 mg of rosuvastatin or a salt thereof.

In an exemplary embodiment, the pharmaceutical composition of the present invention may contain 40 mg of olmesartan medoxomil, 2.5 mg of amlodipine or a salt thereof, and 20 mg of rosuvastatin or a salt thereof.

In yet another exemplary embodiment, the pharmaceutical composition of the present invention may contain 40 mg of olmesartan medoxomil, 2.5 mg of amlodipine or a salt thereof, and 10 mg of rosuvastatin or a salt thereof.

In yet another exemplary embodiment, the pharmaceutical composition of the present invention may contain 20 mg of olmesartan medoxomil, 2.5 mg of amlodipine or a salt thereof, and 10 mg of rosuvastatin or a salt thereof.

In yet another exemplary embodiment, the pharmaceutical composition of the present invention may contain 20 mg of olmesartan medoxomil, 2.5 mg of amlodipine or a salt thereof, and 5 mg of rosuvastatin or a salt thereof.

The pharmaceutical composition according to the present invention may be administered once a day, but is not limited thereto.

Advantageous Effects

According to the present invention, compartments comprising a drug are formulated in separate forms so as to solve problems related to the dissolution and absorption of the drug due to drug interaction, and a biologically equivalent preparation can be obtained when compared to conventional single preparation.

DESCRIPTION OF DRAWINGS

FIG. 1 illustrates the dissolution test results of the preparations of Preparation Examples 7 to 9 in comparison with a reference drug with respect to olmesartan medoxomil.

FIG. 2 illustrates the dissolution test results of the preparations of Preparation Examples 7 to 9 in comparison with a reference drug with respect to amlodipine besylate.

FIG. 3 illustrates the dissolution test results of the preparations of Preparation Examples 7 to 9 in comparison with a reference drug with respect to a rosuvastatin calcium salt.

FIGS. 4 to 6 each illustrate an olmesartan medoxomil blood concentration profile, an amlodipine besylate blood concentration profile, and a rosuvastatin blood concentration profile over time when the bilayer tablet (test drug) of Preparation Example 8 and a reference drug (Sevikar tablet and Crestor tablet) are administered.

FIGS. 7 to 9 each illustrate an olmesartan medoxomil blood concentration profile, an amlodipine besylate blood concentration profile, and a rosuvastatin blood concentration profile over time when the bilayer tablet (test drug) of Preparation Example 15 and a reference drug (Sevikar tablet and Crestor tablet) are administered.

MODES OF THE INVENTION

Examples

Hereinafter, the present invention will be described in more detail in the following Examples. However, the following Examples merely exemplify the content of the present invention, and do not limit or restrict the scope of rights of the present invention. From the detailed description and examples of the present invention, it is understood that what can be easily inferred by a person skilled in the art to which the present invention pertains belongs to the scope of rights of the present invention.

Preparation Examples

Preparation of Bilayer Tablet Including Olmesartan/Amlodipine Layer and Rosuvastatin Layer An olmesartan medoxomil/amlodipine besylate compartment (mixture) and a rosuvastatin calcium compartment (mixture) were prepared according to the compositions of the following table and typical methods.

A composite bilayer tablet including an olmesartan medoxomil/amlodipine compartment (first layer) and a rosuvastatin calcium compartment (second layer) was prepared using a bilayer tablet machine.

EXPERIMENTAL EXAMPLES

Experimental Example 1: Dissolution Test

A comparative dissolution test was performed on the preparations prepared according to the preparation examples of the present invention under the following dissolution test conditions.

As the reference drug used in the comparative dissolution test, a Sevikar™ 10/40 mg tablet (amlodipine besylate/olmesartan medoxomil) and a Crestor™ 20 mg tablet (rosuvastatin calcium) were used.

A Sevikar™ tablet and a Crestor™ tablet are in the form of film-coated single tablets. The Sevikar™ tablet includes silicified microcrystalline cellulose, pregelatinized starch, croscarmellose sodium, and magnesium stearate as an excipient, and includes polyvinyl alcohol, Macrogol/Polyethylene glycol 3350, titanium dioxide, talc, and iron oxide as a film coating agent.

Meanwhile, a Crestor™ tablet includes microcrystalline cellulose, lactose hydrate, tribasic calcium phosphate, crospovidone, and magnesium stearate as an excipient, and includes hypromellose, triacetin, titanium dioxide, and iron oxide as a film coating agent.

[Dissolution Test Conditions]

Dissolution solution: Korean Pharmacopoeia Dissolution Test Method First Liquid, Second Liquid, or Water Olmesartan medoxomil: Water Amlodipine besylate: First liquid, pH 1.2

Rosuvastatin calcium: Second liquid, pH 6.8

Temperature: 37±0.5° C.

Test method: Korean Pharmacopoeia Dissolution Test Method 2 (Paddle method)

Paddle rotation speed: 50 rpm

Analysis method: UPLC method

UPLC Operating Conditions

Column: ACQUITY UPLC BEH C18 (2.1×50 mm 1.7 μm)

Detector: An ultraviolet absorption photometer (239 nm)

Flow rate: 0.1 mL/min

Analysis time: 30 minutes

Mobile phase: Phosphate buffer/Acetonitrile=80/20

Preparation Examples 1 to 6: Preparation of Bilayer Tablet Including Olmesartan/Amlodipine Layer and Rosuvastatin Layer

TABLE 1

| | Ingredient name | Preparation Example 1 | Preparation Example 2 | Preparation Example 3 | Preparation Example 4 | Preparation Example 5 | Preparation Example 6 |
|---|---|---|---|---|---|---|---|
| | Olmesartan medoxomil/amlodipine besylate portion | | | | | | |
| Mixture | Olmesartan medoxomil | 40 | 40 | 40 | 40 | 40 | 40 |
| | Amlodipine besylate | 13.89 | 13.89 | 13.89 | 13.89 | 13.89 | 13.89 |
| | Microcrystalline cellulose | — | — | 92.05 | — | — | — |
| | Silicified microcrystalline cellulose | 92.05 | 92.05 | — | 92.05 | 92.05 | — |
| | Lactose hydrate | — | — | — | — | — | 72.05 |
| | Pregelatinized starch | 40 | — | 40 | 40 | 40 | 40 |
| | Sodium starch glycolate | — | 40 | — | — | — | — |
| | Croscarmellose sodium | 20 | 20 | 10 | 10 | 10 | 15 |
| | Crospovidone | — | — | 20 | — | — | — |
| | Copovidone | — | — | — | 20 | — | — |
| | Carboxymethyl cellulose calcium | — | — | — | — | 20 | — |
| | Low-substituted hydroxypropylcellulose | — | — | — | — | — | 40 |
| | Magnesium stearate | 2 | 2 | 2 | 2 | 2 | 2 |
| | Iron oxide red | 0.06 | 0.06 | 0.06 | 0.06 | 0.06 | 0.06 |
| | Mass(mg) | 208 | 208 | 218 | 218 | 218 | 223 |
| | Rosuvastatin calcium portion | | | | | | |
| Mixture | Rosuvastatin calcium | 20.8 | 20.8 | 20.8 | 20.8 | 20.8 | 20.8 |
| | Lactose hydrate | 126.2 | 126.2 | 116.36 | 116.36 | 116.36 | 116.36 |
| | Microcrystalline cellulose | — | 40 | — | — | — | — |
| | Silicified microcrystalline cellulose | 40 | — | 45.34 | 45.34 | 45.34 | 45.34 |
| | Dibasic calcium phosphate dihydrate | 20 | 20 | 21.8 | 21.8 | 21.8 | 21.8 |
| | Crospovidone | 10 | 10 | 10.7 | 10.7 | 10.7 | 10.7 |
| | Croscarmellose sodium | 5 | 5 | 6.4 | 6.4 | 6.4 | 6.4 |
| | Colloidal silicon oxide | 4 | 4 | 4.3 | 4.3 | 4.3 | 4.3 |
| | Magnesium stearate | 4 | 4 | 4.3 | 4.3 | 4.3 | 4.3 |
| | Mass (mg) | 230 | 230 | 230 | 230 | 230 | 230 |
| Total | Total mass per tablet(mg) | 438 | 438 | 448 | 448 | 448 | 453 |

The dissolution test results of the preparations are shown in the following table.

TABLE 2

| | Olmesartan medoxomil dissolution rate | | | | | | |
|---|---|---|---|---|---|---|---|
| | Dissolution time | | | | | | |
| | 0 minutes | 5 minutes | 10 minutes | 15 minutes | 30 minutes | 45 minutes | 60 minutes |
| Preparation Example 1 | 0 | 45.98 | 69.96 | 79.26 | 89.48 | 93.96 | 95.30 |
| Preparation Example 2 | 0 | 59.12 | 77.07 | 84.37 | 92.96 | 96.31 | 97.79 |
| Preparation Example 3 | 0 | 50.90 | 66.68 | 74.06 | 84.07 | 87.70 | 90.25 |
| Preparation Example 4 | 0 | 49.56 | 69.97 | 80.29 | 92.31 | 96.98 | 97.74 |
| Preparation Example 5 | 0 | 48.84 | 70.94 | 81.10 | 94.01 | 98.37 | 100.99 |
| Preparation Example 6 | 0 | 46.36 | 63.90 | 71.52 | 81.06 | 84.02 | 85.52 |
| Sevikar + Crestor | 0 | 26.32 | 34.05 | 37.96 | 44.78 | 48.49 | 51.23 |

TABLE 3

Amlodipine besylate dissolution rate

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 1 | 0 | 83.28 | 85.47 | 86.48 | 88.41 | 88.38 | 90.20 |
| Preparation Example 2 | 0 | 87.20 | 87.42 | 86.19 | 88.02 | 89.86 | 89.82 |
| Preparation Example 3 | 0 | 87.85 | 89.73 | 90.21 | 91.84 | 93.65 | 95.07 |
| Preparation Example 4 | 0 | 95.39 | 95.11 | 96.88 | 92.41 | 96.42 | 95.60 |
| Preparation Example 5 | 0 | 95.15 | 94.29 | 93.82 | 92.72 | 95.10 | 91.76 |
| Preparation Example 6 | 0 | 86.30 | 91.45 | 91.77 | 92.21 | 92.48 | 94.08 |
| Sevikar + Crestor | 0 | 88.78 | 90.55 | 92.49 | 92.23 | 93.38 | 93.64 |

TABLE 4

Rosuvastatin calcium dissolution rate

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 1 | 0 | 88.91 | 95.19 | 97.18 | 99.82 | 100.23 | 100.43 |
| Preparation Example 2 | 0 | 84.28 | 87.50 | 89.30 | 95.91 | 92.78 | 94.55 |
| Preparation Example 3 | 0 | 84.29 | 88.44 | 89.35 | 92.79 | 94.19 | 94.97 |
| Preparation Example 4 | 0 | 84.60 | 91.66 | 93.61 | 97.26 | 99.54 | 101.71 |
| Preparation Example 5 | 0 | 90.28 | 92.71 | 93.94 | 94.15 | 97.83 | 99.79 |
| Preparation Example 6 | 0 | 87.79 | 90.19 | 91.96 | 91.94 | 94.63 | 95.99 |
| Sevikar + Crestor | 0 | 76.55 | 85.39 | 85.30 | 90.50 | 93.79 | 95.02 |

The preparations of Preparation Examples 1 to 6 had a high dissolution rate of olmesartan in all time slots compared to the reference drug, and the dissolution rate of amlodipine did not have a large deviation as a whole. Meanwhile, the preparations of Preparation Examples 3 to 6 had a slightly higher initial dissolution rate of rosuvastatin than the reference drug, but the deviation from the reference drug was not large as a whole. It was confirmed that the composition of olmesartan/amlodipine may have some influence on the initial dissolution rate of a rosuvastatin layer, but did not have a significant influence on the overall dissolution profile of the rosuvastatin layer.

Preparation Examples 7 to 9: Composition of Bilayer Tablet Including Olmesartan/Amlodipine Layer and Rosuvastatin Layer The following preparations were prepared by changing the types and contents of disintegrants and excipients of the above Preparation Examples.

TABLE 5

Composition of bilayer tablet including olmesartan/amlodipine layer and rosuvastatin layer

| | Ingredient name | Preparation Example 7 | Preparation Example 8 | Preparation Example 9 |
|---|---|---|---|---|
| Olmesartan medoxomil/amlodipine besylate portion | | | | |
| Granule | Olmesartan medoxomil | 40 | 40 | 40 |
| | Amlodipine besylate | 13.89 | 13.89 | 13.89 |
| | Silicified microcrystalline cellulose | 92.05 | 69.05 | 69.05 |
| | Dibasic calcium phosphate dehydrate | — | 40 | — |
| | Anhydrous calcium phosphate | — | — | 40 |

TABLE 5-continued

Composition of bilayer tablet including olmesartan/amlodipine layer and rosuvastatin layer

| Ingredient name | | Preparation Example 7 | Preparation Example 8 | Preparation Example 9 |
|---|---|---|---|---|
| | Pregelatinized starch | 40 | 40 | 40 |
| | Croscarmellose sodium | 20 | 15 | 15 |
| | Crospovidone | 10 | 20 | 20 |
| | Magnesium stearate | 2 | 2 | 2 |
| | Iron oxide red | 0.06 | 0.06 | 0.06 |
| | Mass (mg) | 218 | 240 | 240 |
| Rosuvastatin calcium portion | | | | |
| Mixture | Rosuvastatin calcium | 20.8 | 20.8 | 20.8 |
| | Lactose hydrate | 116.36 | 116.36 | 116.36 |
| | Silicified microcrystalline cellulose | 45.34 | 45.34 | 45.34 |
| | Dibasic calcium phosphate dehydrate | — | 21.8 | 21.8 |
| | Calcium carbonate | 21.8 | — | — |
| | Crospovidone | 10.7 | 10.7 | 10.7 |
| | Croscarmellose sodium | 6.4 | 6.4 | 6.4 |
| | Colloidal silicon oxide | 4.3 | 4.3 | 4.3 |
| | Magnesium stearate | 4.3 | 4.3 | 4.3 |
| | Mass (mg) | 230 | 230 | 230 |
| Total | Total mass per tablet (mg) | 448 | 470 | 470 |

The dissolution test results of the preparations are shown in the following Tables 6 to 8 and FIGS. 1 to 3.

TABLE 6

Olmesartan medoxomil dissolution rate

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 7 | 0 | 30.23 | 48.99 | 59.96 | 76.70 | 84.38 | 88.78 |
| Preparation Example 8 | 0 | 50.56 | 74.05 | 84.45 | 94.83 | 97.27 | 98.75 |
| Preparation Example 9 | 0 | 31.08 | 47.95 | 57.76 | 72.65 | 80.15 | 84.36 |
| Sevikar + Crestor | 0 | 26.32 | 34.05 | 37.96 | 44.78 | 48.49 | 51.23 |

TABLE 7

Amlodipine besylate dissolution rate

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 7 | 0 | 99.98 | 95.79 | 96.37 | 101.28 | 97.84 | 97.62 |
| Preparation Example 8 | 0 | 88.23 | 93.58 | 93.22 | 93.92 | 93.69 | 94.10 |
| Preparation Example 9 | 0 | 93.07 | 91.25 | 93.66 | 96.05 | 96.18 | 95.96 |
| Sevikar + Crestor | 0 | 88.78 | 90.55 | 92.49 | 92.23 | 93.38 | 93.64 |

TABLE 8

| | Rosuvastatin calcium dissolution rate | | | | | |
|---|---|---|---|---|---|---|
| | Dissolution time | | | | | |
| | 0 minutes | 5 minutes | 10 minutes | 15 minutes | 30 minutes | 45 minutes | 60 minutes |
| Preparation Example 7 | 0 | 91.43 | 93.73 | 94.05 | 95.08 | 96.15 | 96.04 |
| Preparation Example 8 | 0 | 89.99 | 92.55 | 93.40 | 94.69 | 95.41 | 95.89 |
| Preparation Example 9 | 0 | 83.86 | 90.55 | 92.80 | 95.07 | 96.26 | 96.78 |
| Sevikar + Crestor | 0 | 76.55 | 85.39 | 85.30 | 90.50 | 93.79 | 95.02 |

The preparations of Preparation Examples 7 to 9 still had a high dissolution rate of olmesartan compared to the reference drug. The dissolution rate of amlodipine showed the lowest deviation from the reference drug in Preparation Example 8 compared to Preparation Examples 7 and 9. The preparations of Preparation Examples 7 to 9 had a slightly higher initial dissolution rate of rosuvastatin than the reference drug, but the deviation from the reference drug was not large as a whole. The preparation of Preparation Example 8 did not have a large deviation in the dissolution rates of amlodipine and rosuvastatin compared to the reference drug, and thus showed the most similar dissolution rate compared to the reference drug among the preparations. Considering that the dissolution rate of the preparation of Preparation Example 8 is good, it was determined that dibasic calcium phosphate dihydrate plays an important role in the dissolution rate of the preparation. Meanwhile, the preparation of Preparation Example 9 had an olmesartan dissolution rate similar to that of the preparation of Preparation Example 7, and the deviation from the reference drug was shown to be at a level of 15%. The preparation of Preparation Example 9 had a smaller deviation from the reference drug than the preparation of Preparation Example 8 having a deviation of 30% or more from the reference drug. Further, in terms of the dissolution rates of amlodipine and rosuvastatin, the preparation of Preparation Example 9 had a less deviation from the reference drug than the preparation of Preparation Example 7. Therefore, an experiment of bioequivalence was performed on the preparations of Preparation Examples 8 and 9.

In general, the Ministry of Food and Drug Safety Notification No. 2017-28, Chapter 3, Article 21 is referenced for the similarity judgment of the comparative dissolution test. In the case of olmesartan, the average dissolution rate of the reference drug is less than 50% within the specified test time, so it is determined that the dissolution rate is equivalent when the dissolution rate deviation is within ±8% or the similarity factor (f2) value is 55 or more. It can be seen that in the preparations of Preparation Examples 1 to 9, the elution rate of olmesartan is not equivalent to that of the reference drug, and a deviation of 30% or more from that of the reference drug occurs. In the case of amlodipine and rosuvastatin, the average dissolution rate of the reference drug is 85% or more within 15 minutes, so a dissolution rate deviation within ±15% can be judged to be equivalent.

Preparation Examples 8A and 8B: Preparation of Coated Tablet

Coated tablets of Preparation Examples 8A and 8B were prepared by coating the naked tablets prepared according to Preparation Example 8 with a coating material of the following composition.

TABLE 9

Composition of bilayer coated tablet including olmesartan/amlodipine layer and rosuvastatin layer

| Ingredient name | Preparation Example 8A | Preparation Example 8B |
|---|---|---|
| Olmesartan medoxomil/amlodipine besylate portion | | |
| Olmesartan medoxomil | 40.00 | 40.00 |
| Amlodipine besylate | 13.89 | 13.89 |
| Silicified microcrystalline cellulose | 69.05 | 69.05 |
| Dibasic calcium phosphate dihydrate | 40.00 | 40.00 |
| Pregelatinized starch | 40.00 | 40.00 |
| Croscarmellose sodium | 15.00 | 15.00 |
| Crospovidone | 20.00 | 20.00 |
| Magnesium stearate | 2.00 | 2.00 |
| Iron oxide red | 0.06 | 0.06 |
| Olmesartan medoxomil/amlodipine besylate portion mass (mg) | 240.00 | 240.00 |
| Rosuvastatin calcium portion | | |
| Rosuvastatin calcium | 20.80 | 20.80 |
| Lactose hydrate | 116.36 | 116.36 |
| Silicified microcrystalline cellulose | 45.34 | 45.34 |
| Dibasic calcium phosphate dihydrate | 21.80 | 21.80 |
| Crospovidone | 10.70 | 10.70 |
| Croscarmellose sodium | 6.40 | 6.40 |
| Colloidal silicon oxide | 4.30 | 4.30 |
| Magnesium stearate | 4.30 | 4.30 |
| Rosuvastatin calcium portion mass (mg) | 230.00 | 230.00 |
| Total mass per tablet (naked tablet) (mg) | 470.00 | 470.00 |
| Coating material | | |
| PVA | 15.00 | — |
| PVA copolymer (PVA/macrogol grafted polymer) | — | 15.00 |
| Total mass per tablet (coated tablet) (mg) | 485.00 | 485.00 |

The dissolution test results of the preparations of Preparation Examples 8A and 8B were similar to the dissolution test results of the preparation of Preparation Example 8.

Experimental Example 2: Bioequivalence Test

Bioequivalence with the reference drug was evaluated by performing a pharmacokinetic test (PK test) on the preparation of Preparation Example 8.

That is, 64 healthy male volunteers were divided into two groups of 32 each, the tablet of Preparation Example 8 was orally administered to the first group, and the Sevikar 10/40 mg tablet (amlodipine besylate/olmesartan medoxomil) and the Crestor 20 mg tablet were orally administered in combination to the second group. Blood was collected at 0, 0, 5, 1, 5, 2, 2, 5, 3, 4, 5, 6, 8, 10, 12, 16, 24, 48, and 72 hours after administration, and the blood concentrations of olmesartan, amlodipine, and rosuvastatin were each quantified using UPLC-MS/MS (Waters ACQUITY UPLC™ system). After quantification, bioequivalence between the preparations was evaluated by statistically processing the AUC and Cmax of olmesartan, amlodipine, and rosuvastatin at the time of administration of the reference drug (combination administration) and the test drug.

The evaluation of bioequivalence was performed in accordance with the Bioequivalence Standards Guidelines of the Ministry of Food and Drug Safety. That is, after the AUC and Cmax values of olmesartan, amlodipine and rosuvastatin were log-transformed, a geometric mean was obtained and the projected 90% confidence intervals for the geometric mean ratio were calculated. It is acknowledged that two preparations are biologically equivalent when the 90% confidence interval is 0.8 to 1.25.

The blood concentration profiles obtained by the PK test are shown in FIGS. 4 to 6. FIGS. 4 to 6 each illustrate an olmesartan medoxomil blood concentration profile, an amlodipine besylate blood concentration profile, and a rosuvastatin blood concentration profile over time when the bilayer tablet (test drug) of Preparation Example 8 and a reference drug (Sevikar tablet and Crestor tablet) are administered.

The results of the bioequivalence evaluation performed as described above are shown in the following Table 10. In Table 10, a T/R ratio was obtained by dividing the geometric mean of the evaluation items for the test preparation by the geometric mean of the evaluation items for the control preparation [that is, T/R ratio=the geometric mean of the evaluation items (test preparation)/the geometric mean of the evaluation items (control preparation)]. A T/R ratio higher than 1 means that the test drug absorbs more than the reference drug on average, and the maximum blood concentration of the test drug is higher than the reference drug on average, and a T/R ratio less than 1 means that the test drug is absorbed less than the reference drug on average, or the blood concentration of the test drug is lower than that of the reference drug on average. That is, the farther the T/R ratio is from 1, the higher the probability it is determined to be biologically non-equivalent.

TABLE 10

PK of bilayer tablet of Preparation Example 8

| Ingredient | PK parameter | 90% confidence interval (T/R ratio) |
|---|---|---|
| Olmesartan | AUC | 0.9716-1.0578 (1.0138) |
|  | Cmax | 0.9818-1.1009 (1.0396) |
| Amlodipine | AUC | 1.0243-1.0757 (1.0497) |
|  | Cmax | 1.0369-1.1074 (1.0716) |
| Rosuvastatin | AUC | 0.9453-1.0669 (1.0043) |
|  | Cmax | 0.9433-1.1152 (1.0257) |

In addition, bioequivalence with the reference drug was evaluated by performing a pharmacokinetic test (PK test) on the preparation of Preparation Example 9 in beagle dogs. That is, 32 beagle dogs were divided into two groups of 16 each, the tablet of Preparation Example 9 was orally administered to the first group, and of the Sevikar 10/40 mg tablet (amlodipine besylate/olmesartan medoxomil) and the Crestor 20 mg tablet were orally administered to the second group. After administration, the blood concentrations were each quantified in the same manner as in the above PK test method, and then the bioequivalence between the preparations was evaluated by statistically processing the AUC and Cmax at the time of administration of the reference drug (combination administration) and the test drug. The results of the bioequivalence evaluation performed as described above are shown in the following Table 11.

TABLE 11

PK of bilayer tablet of Preparation Example 9

| Ingredient | PK parameter | 90% confidence interval (T/R ratio) |
|---|---|---|
| Olmesartan | AUC | 0.8223-1.0312 (0.92) |
|  | Cmax | 0.7924-1.0178 (0.898) Non-equivalent |
| Amlodipine | AUC | 0.9207-1.0624 (0.988) |
|  | Cmax | 0.8535-1.0658 (0.953) |
| Rosuvastatin | AUC | 0.7891-1.0523 (0.911) Non-equivalent |
|  | Cmax | 0.6577-0.9303 (0.782) Non-equivalent |

Experimental Example 3: Comparison of Sizes of Final Tablets

The total weight of a Sevikar 10/40 mg tablet and of a Crestor 20 mg tablet used as a reference drug was 208 mg and 309 mg, respectively. The total weight of the bilayer tablet of Preparation Example 8 according to the present invention was 470 mg, which was smaller in total weight and smaller in size than the combination of the Sevikar tablet and the Crestor tablet, so that the dosing convenience for patients was enhanced.

Preparation Examples 10 to 14: Preparation of Low-Dose Bilayer Tablets

Based on the composition of the coated tablet of Preparation Example 8, bilayer tablets of Preparation Examples 10 to 14 having the following composition were prepared.

TABLE 12

Composition of bilayer tablet including olmesartan/amlodipine layer and rosuvastatin layer

| | Ingredient name | Preparation Example 10 | Preparation Example 11 | Preparation Example 12 | Preparation Example 13 | Preparation Example 14 |
|---|---|---|---|---|---|---|
| Olmesartan medoxomil/amlodipine besylate portion |||||||
| Granule | Olmesartan medoxomil | 40 | 40 | 40 | 20 | 20 |
|  | Amlodipine besylate | 13.89 | 6.945 | 6.945 | 6.945 | 6.945 |
|  | Silicified microcrystalline cellulose | 69.05 | 75.995 | 75.995 | 34.525 | 34.525 |

TABLE 12-continued

Composition of bilayer tablet including olmesartan/amlodipine layer and rosuvastatin layer

|  | Ingredient name | Preparation Example 10 | Preparation Example 11 | Preparation Example 12 | Preparation Example 13 | Preparation Example 14 |
| --- | --- | --- | --- | --- | --- | --- |
|  | Dibasic calcium phosphate dihydrate | 40 | 40 | 40 | 20 | 20 |
|  | Pregelatinized starch | 40 | 40 | 40 | 20 | 20 |
|  | Croscarmellose sodium | 15 | 15 | 15 | 7.5 | 7.5 |
|  | Crospovidone | 20 | 20 | 20 | 10 | 10 |
|  | Magnesium stearate | 2 | 2 | 2 | 1 | 1 |
|  | Iron oxide red | 0.06 | 0.06 | 0.06 | 0.03 | 0.03 |
|  | Mass(mg) | 240 | 240 | 240 | 120 | 120 |
|  | Rosuvastatin calcium portion | | | | | |
| Granule | Rosuvastatin calcium | 10.4 | 10.4 | 5.2 | 10.4 | 5.2 |
|  | Lactose hydrate | 58.18 | 58.18 | 29.09 | 58.18 | 29.09 |
|  | Silicified microcrystalline cellulose | 22.67 | 22.67 | 11.335 | 22.67 | 11.335 |
|  | Dibasic calcium phosphate dihydrate | 10.9 | 10.9 | 5.45 | 10.9 | 5.45 |
|  | Crospovidone | 5.35 | 5.35 | 2.675 | 5.35 | 2.675 |
|  | Croscarmellose sodium | 3.2 | 3.2 | 1.6 | 3.2 | 1.6 |
|  | Colloidal silicon oxide | 2.15 | 2.15 | 1.575 | 2.15 | 1.575 |
|  | Magnesium stearate | 2.15 | 2.15 | 1.575 | 2.15 | 1.575 |
|  | Mass (mg) | 115 | 115 | 58.5 | 115 | 58.5 |
| Total | Total mass per tablet(mg) | 355 | 355 | 298.5 | 235 | 178.5 |

The dissolution test results of the preparations of Preparation Examples 10 to 14 are shown in the following Tables 13 to 15.

TABLE 13

Olmesartan medoxomil (pH 6.8)

| | Dissolution time | | | | | |
| --- | --- | --- | --- | --- | --- | --- |
| | 0 minutes | 5 minutes | 10 minutes | 15 minutes | 30 minutes | 45 minutes | 60 minutes |
| Preparation Example 8 | 0 | 46.78 | 66.96 | 77.30 | 90.09 | 95.87 | 99.60 |
| Preparation Example 10 | 0 | 48.80 | 69.46 | 78.63 | 89.86 | 94.72 | 97.37 |
| Preparation Example 11 | 0 | 46.41 | 68.27 | 77.83 | 89.06 | 93.71 | 96.32 |
| Preparation Example 12 | 0 | 50.70 | 70.48 | 84.03 | 94.04 | 98.24 | 100.35 |
| Preparation Example 13 | 0 | 50.56 | 70.56 | 84.44 | 95.36 | 98.58 | 102.95 |
| Preparation Example 14 | 0 | 51.22 | 71.80 | 85.51 | 95.60 | 98.81 | 102.62 |

TABLE 14

Amlodipine besylate (pH 1.2)

| | Dissolution time | | | | | |
| --- | --- | --- | --- | --- | --- | --- |
| | 0 minutes | 5 minutes | 10 minutes | 15 minutes | 30 minutes | 45 minutes | 60 minutes |
| Preparation Example 8 | 0 | 83.73 | 89.54 | 91.52 | 93.90 | | |
| Preparation Example 10 | 0 | 84.10 | 87.36 | 89.11 | 90.62 | | |
| Preparation Example 11 | 0 | 85.83 | 89.52 | 89.10 | 91.34 | | |

TABLE 14-continued

Amlodipine besylate (pH 1.2)

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 12 | 0 | 84.55 | 86.66 | 88.23 | 92.84 | | |
| Preparation Example 13 | 0 | 85.27 | 87.90 | 89.83 | 90.76 | | |
| Preparation Example 14 | 0 | 83.42 | 89.13 | 90.66 | 93.71 | | |

TABLE 15

Rosuvastatin calcium (pH 6.8)

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 8 | 0 | 99.82 | 100.76 | 101.65 | | | |
| Preparation Example 10 | 0 | 100.51 | 101.74 | 101.91 | | | |
| Preparation Example 11 | 0 | 99.73 | 100.22 | 101.40 | | | |
| Preparation Example 12 | 0 | 99.52 | 100.58 | 101.24 | | | |
| Preparation Example 13 | 0 | 100.80 | 102.69 | 103.31 | | | |
| Preparation Example 14 | 0 | 97.81 | 98.80 | 99.33 | | | |

The preparations of Preparation Examples 10 to 14 are preparations in which raw material drugs of the preparation of Preparation Example 8 and amounts thereof have been changed. It can be seen that the dissolution rates of the olmesartan, amlodipine, and rosuvastatin ingredients are the same in the specific eluate for each ingredient, despite the change in the raw material drugs and amounts thereof.

Preparation Examples 15 and 16: Preparation of Low-Dose Bilayer Tablets

Based on the composition of the coated tablet of Preparation Example 8, bilayer tablets of Preparation Examples 15 and 16 having the following composition were prepared.

TABLE 16

Composition of bilayer tablet including olmesartan/amlodipine layer and rosuvastatin layer

| | Ingredient name | Preparation Example 15 | Preparation Example 16 |
|---|---|---|---|
| Olmesartan medoxomil/amlodipine besylate portion | | | |
| Granule | Olmesartan medoxomil | 40 | 40 |
| | Amlodipine besylate | 6.95 | 6.95 |
| | Silicified microcrystalline cellulose | 55 | 55 |
| | Dibasic calcium phosphate dihydrate | 36 | 36 |
| | Pregelatinized starch | 40 | 40 |
| | Croscarmellose sodium | 15 | 15 |
| | Crospovidone | 20 | 20 |

TABLE 16-continued

Composition of bilayer tablet including olmesartan/amlodipine layer and rosuvastatin layer

| | Ingredient name | Preparation Example 15 | Preparation Example 16 |
|---|---|---|---|
| | Magnesium stearate | 2 | 2 |
| | Iron oxide red | 0.05 | 0.05 |
| | Mass | 215 | 215 |
| Rosuvastatin calcium portion | | | |
| Granule | Rosuvastatin calcium | 10.4 | 5.2 |
| | Lactose hydrate | 73.00 | 36.5 |
| | Silicified microcrystalline cellulose | 26.50 | 13.25 |
| | Dibasic calcium phosphate dihydrate | 21.80 | 10.9 |
| | Crospovidone | 7 | 3.5 |
| | Croscarmellose sodium | 5 | 2.5 |
| | Colloidal silicon oxide | 2.15 | 1.075 |
| | Magnesium stearate | 2.15 | 1.075 |
| | Mass (mg) | 148 | 74 |
| Total | Total mass per tablet | 363 | 289 |

Experimental Example 4: Dissolution Test

Using Preparation Example 15 and a Servikar™ 5/40 mg tablet (amlodipine besylate/olmesartan medoxomil) and a Crestor™ 10 mg tablet (rosuvastatin calcium) as reference drugs, a comparative dissolution test was performed by the method of Experimental Example 1.

The comparative dissolution test results are shown in the following Tables 17 to 19.

TABLE 17

Olmesartan medoxomil dissolution rate (water)

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 15 | 0 | 58.47 | 77.55 | 85.80 | 94.70 | 97.23 | 98.56 |
| Sevikar + Crestor | 0 | 16.86 | 21.64 | 24.53 | 29.35 | 31.34 | 32.55 |

TABLE 18

Amlodipine besylate dissolution rate (pH 1.2)

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 15 | 0 | 89.89 | 92.78 | 92.73 | 93.37 | 93.15 | 92.63 |
| Sevikar + Crestor | 0 | 91.02 | 92.78 | 92.73 | 93.37 | 93.15 | 92.63 |

TABLE 19

Rosuvastatin calcium dissolution rate (pH 6.8)

| | Dissolution time | | | | | |
|---|---|---|---|---|---|---|
| | 0 minutes | 5 minutes | 10 minutes | 15 minutes | 30 minutes | 45 minutes | 60 minutes |
| Preparation Example 15 | 0 | 92.17 | 95.53 | 96.56 | 97.61 | 98.46 | 98.85 |
| Sevikar + Crestor | 0 | 83.55 | 87.93 | 88.93 | 91.01 | 92.93 | 93.94 |

The preparation of Preparation Example 15 still had a high dissolution rate of olmesartan compared to the reference drug, and did not have a large deviation in dissolution rate of amlodipine and rosuvastatin from that of the reference drug, and showed a dissolution rate similar to that of the reference drug.

Experimental Example 5: Bioequivalence Test

Bioequivalence with the reference drug was evaluated by performing a pharmacokinetic test (PK test) on the preparation of Preparation Example 15.

That is, 64 healthy male volunteers were divided into two groups of 32 each, the tablet of Preparation Example 15 was orally administered to the first group, and a Sevikar 5/40 mg tablet (amlodipine besylate/olmesartan medoxomil) and a Crestor 20 mg tablet were orally administered in combination to the second group. Blood was collected at 0, 0.5, 1.5, 2, 2.5, 3, 4, 5, 6, 8, 10, 12, 16, 24, 48, and 72 hours after administration, and the blood concentrations of olmesartan, amlodipine, and rosuvastatin were each quantified using the UPLC-MS/MS (Waters ACQUITY UPLC™ system). After quantification, bioequivalence between the preparations was evaluated by statistically processing the AUC and Cmax of olmesartan, amlodipine, and rosuvastatin at the time of administration of the reference drug (combination administration) and the test drug.

The evaluation of bioequivalence was performed in accordance with the Bioequivalence Standards Guidelines of the Ministry of Food and Drug Safety. That is, after the AUC and Cmax values of olmesartan, amlodipine and rosuvastatin were log-transformed, a geometric mean was obtained and the projected 90% confidence intervals for the geometric mean ratio were calculated. It is acknowledged that two preparations are biologically equivalent when the 90% confidence interval is 0.8 to 1.25.

The blood concentration profiles obtained by the PK test are shown in FIGS. 7 to 9. FIGS. 7 to 9 each illustrate an olmesartan medoxomil blood concentration profile, an amlodipine besylate blood concentration profile, and a rosuvastatin blood concentration profile over time when the bilayer tablet (test drug) of Preparation Example 15 and a reference drug (Sevikar tablet and Crestor tablet) are administered.

The results of the bioequivalence evaluation performed as described above are shown in the following Table 20. In Table 20, a T/R ratio was obtained by dividing the geometric mean of the evaluation items for the test preparation by the geometric mean of the evaluation items for the control preparation [that is, T/R ratio=the geometric mean of the evaluation items (test preparation)/the geometric mean of the evaluation items (control preparation)]. A T/R ratio higher than 1 means that the test drug absorbs more than the reference drug on average, and the maximum blood concentration of the test drug is higher than the reference drug on average, and a T/R ratio less than 1 means that the test drug is absorbed less than the reference drug on average, or the blood concentration of the test drug is lower than that of the reference drug on average. That is, the farther the T/R ratio is from 1, the higher the probability it is determined to be biologically non-equivalent.

TABLE 20

PK of bilayer tablet of Preparation Example 15

| Ingredient | PK parameter | 90% confidence interval (T/R ratio) |
| --- | --- | --- |
| Olmesartan | AUC | 0.9351-1.0170 (0.9752) |
|  | Cmax | 0.9304-1.0491 (0.9880) |
| Amlodipine | AUC | 1.0054-1.0526 (1.0287) |
|  | Cmax | 1.0064-1.0696 (1.0375) |
| Rosuvastatin | AUC | 0.9644-1.0834 (1.0222) |
|  | Cmax | 0.9857-1.1518 (1.0655) |

The invention claimed is:

1. A pharmaceutical composition of a single dosage form, comprising: a compartment comprising olmesartan medoxomil and amlodipine or a salt thereof; and a compartment comprising rosuvastatin or a salt thereof, wherein the pharmaceutical composition has a dosage form of a bilayer tablet comprising a layer containing olmesartan medoxomil and amlodipine or a salt thereof and a layer containing rosuvastatin or a salt thereof, wherein the compartment comprising olmesartan medoxomil and amlodipine or a salt thereof contains dibasic calcium phosphate dihydrate in an amount of 1 to 30 parts by weight based on total 100 parts by weight of the compartment comprising olmesartan medoxomil and amlodipine or a salt thereof;

wherein the compartment comprising olmesartan medoxomil and amlodipine or a salt thereof comprises pregelatinized starch, croscarmellose sodium, and crospovidone as disintegrants, wherein the disintegrants are in amounts of 4 to 40 parts by weight, 1 to 10 parts by weight, and 1 to 20 parts by weight, respectively, based on 100 parts by weight of the compartment, wherein the compartment comprising rosuvastatin or a salt thereof comprises crospovidone and croscarmellose sodium as disintegrants, wherein the disintegrants are each in an amount of 1 to 10 parts by weight based on total 100 parts by weight of the compartment.

2. The pharmaceutical composition of claim 1, wherein the pharmaceutical composition is a bilayer tablet coated with a coating agent.

3. The pharmaceutical composition of claim 2, wherein the pharmaceutical composition is a bilayer tablet coated with polyvinyl alcohol or a polyvinyl alcohol copolymer.

4. The pharmaceutical composition of claim 1, wherein the salt of amlodipine is amlodipine besylate.

5. The pharmaceutical composition of claim 1, wherein the salt of rosuvastatin is a rosuvastatin calcium salt.

6. The pharmaceutical composition of claim 1, wherein D(90) of olmesartan medoxomil is 5 to 45 μm.

7. The pharmaceutical composition of claim 1, wherein D(90) of amlodipine or a salt thereof is 5 to 100 μm.

8. The pharmaceutical composition of claim 1, wherein D(90) of rosuvastatin or a salt thereof is 5 to 50 μm.

9. The pharmaceutical composition of claim 1, wherein the pharmaceutical composition is for the treatment or prevention of essential hypertension and hyperlipidemia.

10. The pharmaceutical composition of claim 1, wherein the pharmaceutical composition is for administration to a patient who requires combined therapy of amlodipine and olmesartan medoxomil and simultaneously needs to be administered rosuvastatin.

11. The pharmaceutical composition of claim 1, wherein the pharmaceutical composition comprises olmesartan medoxomil, amlodipine, and rosuvastatin in the following doses based on a unit preparation:

40 mg of olmesartan medoxomil, 10 mg of amlodipine or a salt thereof, and 20 mg of rosuvastatin or a salt thereof;

40 mg of olmesartan medoxomil, 10 mg of amlodipine or a salt thereof, and 10 mg of rosuvastatin or a salt thereof;

40 mg of olmesartan medoxomil, 5 mg of amlodipine or a salt thereof, and 10 mg of rosuvastatin or a salt thereof;

40 mg of olmesartan medoxomil, 5 mg of amlodipine or a salt thereof, and 5 mg of rosuvastatin or a salt thereof;

20 mg of olmesartan medoxomil, 5 mg of amlodipine or a salt thereof, and 10 mg of rosuvastatin or a salt thereof;

20 mg of olmesartan medoxomil, 5 mg of amlodipine or a salt thereof, and 5 mg of rosuvastatin or a salt thereof;

40 mg of olmesartan medoxomil, 2.5 mg of amlodipine or a salt thereof, and 20 mg of rosuvastatin or a salt thereof;

40 mg of olmesartan medoxomil, 2.5 mg of amlodipine or a salt thereof, and 10 mg of rosuvastatin or a salt thereof;

20 mg of olmesartan medoxomil, 2.5 mg of amlodipine or a salt thereof, and 10 mg of rosuvastatin or a salt thereof, or 20 mg of olmesartan medoxomil, 2.5 mg of amlodipine or a salt thereof, and 5 mg of rosuvastatin or a salt thereof.

* * * * *